(12) United States Patent
Clark et al.

(10) Patent No.: US 8,100,981 B2
(45) Date of Patent: Jan. 24, 2012

(54) TIBIAL PROSTHESIS

(75) Inventors: Ron Clark, Valparaiso, IN (US); David Blakemore, Warsaw, IN (US); Ross Mack, Valparaiso, IN (US)

(73) Assignee: VOT, LLC, Warsaw, IN (US)

( * ) Notice: Subject to any disclaimer, the term of this patent is extended or adjusted under 35 U.S.C. 154(b) by 227 days.

(21) Appl. No.: 12/393,682

(22) Filed: Feb. 26, 2009

(65) Prior Publication Data

US 2009/0228112 A1  Sep. 10, 2009

Related U.S. Application Data

(60) Provisional application No. 61/067,740, filed on Feb. 29, 2008, provisional application No. 61/067,741, filed on Feb. 29, 2008, provisional application No. 61/067,742, filed on Feb. 29, 2008.

(51) Int. Cl.
*A61F 2/38* (2006.01)
(52) U.S. Cl. ........................... 623/20.32; 623/20.3
(58) Field of Classification Search ....... 623/20.3–20.34
See application file for complete search history.

(56) References Cited

U.S. PATENT DOCUMENTS

| | | |
|---|---|---|
| 4,166,292 A | 9/1979 | Bokros |
| 4,778,473 A | 10/1988 | Matthews et al. |
| 4,963,152 A | 10/1990 | Hofmann et al. |
| 5,171,276 A | 12/1992 | Caspari et al. |
| 5,266,075 A | 11/1993 | Clark et al. |
| 5,336,266 A | 8/1994 | Caspari et al. |
| 5,393,302 A | 2/1995 | Clark et al. |
| 5,405,395 A | 4/1995 | Coates |
| 5,643,273 A | 7/1997 | Clark |
| 5,766,256 A | 6/1998 | Oudard et al. |
| 5,954,747 A | 9/1999 | Clark |
| 6,306,138 B1 | 10/2001 | Clark et al. |
| 6,306,156 B1 | 10/2001 | Clark |
| 6,423,096 B1 | 7/2002 | Musset et al. |
| 6,558,389 B2 | 5/2003 | Clark et al. |
| 6,723,102 B2 | 4/2004 | Johnson et al. |
| 6,780,188 B2 | 8/2004 | Clark et al. |
| 6,821,300 B2 | 11/2004 | Masini |
| 6,884,246 B1 | 4/2005 | Sonnabend et al. |
| 6,923,817 B2 | 8/2005 | Carson et al. |
| 6,966,928 B2 | 11/2005 | Fell et al. |
| 7,083,652 B2 | 8/2006 | McCue et al. |
| 7,105,027 B2 | 9/2006 | Lipman et al. |
| 7,141,053 B2 | 11/2006 | Rosa et al. |
| 7,297,164 B2 | 11/2007 | Johnson et al. |
| 2002/0161448 A1 | 10/2002 | Hayes, Jr. et al. |

(Continued)

OTHER PUBLICATIONS

International Search Report and Written Opinion dated May 26, 2009 in PCT Application No. PCT/US09/35304.

(Continued)

*Primary Examiner* — David H Willse
*Assistant Examiner* — Javier Blanco
(74) *Attorney, Agent, or Firm* — Heslin Rothenberg Farley & Mesiti P.C.

(57) ABSTRACT

The present invention relates to a tibial prosthesis useful in knee replacement surgeries. The prosthesis includes one or more cement introduction ports which may be used to deliver and control delivery of bone cement to a prosthesis-bone interface after the prosthesis has been positioned on a resurfaced area of a tibia bone. The prosthesis is suitable for implantation using arthroscopic as well as open surgical procedures. The prosthesis may be used as a unicondylar implant in either compartment of the knee or in both compartments of the knee.

11 Claims, 3 Drawing Sheets

U.S. PATENT DOCUMENTS

| | | |
|---|---|---|
| 2003/0009232 A1 | 1/2003 | Metzger et al. |
| 2004/0167631 A1 | 8/2004 | Luchesi et al. |
| 2004/0243134 A1 | 12/2004 | Walker et al. |
| 2005/0192583 A1 | 9/2005 | Walker et al. |
| 2005/0192584 A1 | 9/2005 | Walker et al. |
| 2005/0283253 A1 | 12/2005 | Coon et al. |
| 2006/0052875 A1 | 3/2006 | Bernero et al. |
| 2006/0235537 A1 | 10/2006 | Kuczynski et al. |
| 2007/0005142 A1 | 1/2007 | Rhodes et al. |
| 2007/0032876 A1 | 2/2007 | Clark |
| 2007/0198022 A1 | 8/2007 | Lang et al. |
| 2007/0213735 A1 | 9/2007 | Saadat et al. |
| 2007/0288029 A1 | 12/2007 | Justin et al. |
| 2007/0299532 A1 | 12/2007 | Rhodes et al. |

OTHER PUBLICATIONS

International Search Report and Written Opinion dated Jun. 2, 2009 in PCT Application No. PCT/US09/35301.

U.S. Appl. No. 12/393,658, filed Feb. 26, 2009.

TIBIAL PROSTHESIS

This application claims the benefit of U.S. Provisional Application Ser. No. 61/067,740 filed Feb. 29, 2008; U.S. Provisional Application Ser. No. 61/067,741 filed Feb. 29, 2008; and U.S. Provisional Application Ser. No. 61/067,742 filed Feb. 29, 2008, the entire disclosure of each of which is incorporated herein by this specific reference.

The present invention generally relates to prosthetic implants and, more particularly, to tibial prostheses for human knee joints.

BACKGROUND OF THE INVENTION

It has become a common practice to implant medical prostheses to resurfaced articular surfaces of knees, for example, during knee replacement surgery. Many of the prior art prosthetic implants require large incisions to provide adequate access to the joint space to accommodate the implant as well as the surgical tools required during the surgery. In addition, conventional knee replacement procedures often involve resection or removal of substantial amount of bone or cartilage tissue in order to accommodate the relatively large prosthetic implant designs typically used today. Such substantial removal of bone can cause increased surgical trauma to a patient and may increase time required for recovery and rehabilitation. In addition, excessive removal of bone tissue may lead to failure of the prosthetic implant due to subsidence thereof into the underlying bone tissue. Unfortunately, this often necessitates additional surgery, for example, revision surgery, in order to replace the failed implant.

Bone cement is typically used to secure implant components to a resurfaced bone. Misalignment of components may occur when too much or too little bone cement is placed on the implant and the implant positioned on the bone surface. If excess bone cement is used, bone cement may escape from between the bone and the edges of the implant requiring additional surgical steps or processes to remove the escaped cement. Alternatively, if too little bone cement is used, the inadequate amounts of bone cement may result in inadequate fixation of the implant to the bone, resulting in the loosening of the implant, necessitating revision surgery to correct.

Caspari et al U.S. Pat. No. 5,336,266 discloses tibial and femoral knee joint prosthesis which include open channels through which bone cement can be passed to an inner surface of the implant to at least assist in fixing the implant to the tibia/femur bone. Caspari et al discloses a two piece tibial implant including a polymeric insert fitted into a metal implant body. Caspari et al employs a sharp rim on the implant to form a seal around the cement receiving chamber. In spite of such structure, the Caspari et al devices tend to have problems, for example, with cement leakage, too much or too little cement being injected, uneven distribution of the cement, which can cause discomfort and/or other harm to the patient and/or revision surgery.

There is still an unmet need for better prosthetic implants, for example, tibial prosthetic implants useful in knee replacement surgery.

SUMMARY OF THE INVENTION

Accordingly, it is an object of the present invention to overcome at least some of the above-mentioned disadvantages associated with prior art devices and surgical procedures. The present invention provides new, for example, improved or enhanced, tibial prosthesis devices for a human knee joint, and which may be, and preferably are, structured to be implantable by means of arthroscopic surgical techniques as well as conventional, open surgical techniques. The present prosthetic devices may be used as unicondylar implants in either compartment of the knee or in both compartments of the knee.

Advantageously, the present devices may be sized and structured to reduce the required size of surgical incisions and/or reduce the amount of bone that must be removed during surgery, when compared to prior art implant devices and surgical procedures.

The present devices may be structured to prohibit or substantially prevent or reduce undesirable leakage of bone cement away from the implant, for example, leakage of bone cement into a joint space adjacent the implant. For example, the device may include structure effective to facilitate delivery of bone cement to the appropriate interface region between the implant device and the resurfaced region of the bone, for example, the tibia bone.

The devices of the invention may be structured to reduce occurrence of subsidence of the implant device. For example, the devices may be structured to require or to be used in combination with no more than a minimal, or substantially a minimal, resection of bone such that bone architecture is left substantially intact and better able to adequately support the implants. In one embodiment, the present devices may be used with less resection of bone relative to another implant device, for example, an identical implant device, without one or more of the structural features of the present devices.

Another object of the present invention is to reduce surgical trauma by providing devices, for example, tibial prostheses, that reduce the required size of surgical incisions and/or that reduce the amount of bone that must be removed during implantation when compared to prior art tibial prosthetic devices or identical prosthetic devices which are without one or more structural features of the present devices. Advantageously, the present devices may be surgically implanted into an articular surface of a knee using either conventional open surgical methods or arthroscopic surgical methods. In some preferred embodiments of the invention, the devices comprise tibial prostheses which are structured, for example, sized, shaped or otherwise configured, to be implantable through a single surgical incision, or skin portal, which may be less than about 40 mm, or less than about 30 mm or less than about 25 mm.

Yet another object of the present invention is to provide an implant that, in the event that revision surgery is required, would allow the use of a standard unicompartment replacement knee prosthesis. In one aspect of the invention, the present implant devices are structured to require a minimal or substantially minimal resection of bone such that the bone architecture is left substantially intact leaving more bone stock available for use in revision surgery when compared to prior art devices or identical prosthetic devices which are without one or more structural features of the present devices, and prior art surgical procedures.

Accordingly, prosthetic implants, for example, tibial prosthesis devices, are provided. In one useful aspect of the invention, the devices useful in knee replacement surgery comprise a proximal articulating region, hereinafter sometimes referred to a proximal region; and a distal fixation region, hereinafter sometimes referred to as a distal region, substantially opposing the proximal region and structured to substantially interface with a resurfaced region of a bone, such as a tibia bone. The proximal region provides a prosthetic articulating surface of a resurfaced bone, for example, a resurfaced tibia bone. The distal region, substantially opposing the proximal region, is generally structured to substantially interface with a resurfaced region of a bone, for example, a tibia bone, and may be implanted on or into a resurfaced region of a bone, for example, a tibia bone.

In one embodiment, the present tibial prosthetic devices include a peripheral sidewall between the proximal region and the distal region and including a substantially straight sidewall portion and a curved or substantially curved sidewall portion, so as to form a somewhat semi-circular or D-shaped configuration of the device, and defining an area approximating a resurfaced area of a tibia bone.

The present prosthetic devices may be structured to be effective to facilitate introduction of and effective containment of bone cement used to bond the device to a resurfaced region of a bone, for example, a tibia bone. For example, at least one port may be positioned and structured for receiving and passing bone cement introduced or injected through the port or ports during the surgical procedure, for example, after the device is placed in contact with or on the tibia bone. Further, the present devices may be structured to facilitate containing the bone cement and substantially preventing undesirable leakage thereof into the joint space. For example, the device may be structured to prevent undesirable extrusion of cement exterior to the device after implantation of the device.

In one aspect of the invention, the present prosthetic devices comprise at least one port, for example, defined by a bore, positioned to facilitate introduction or injection of bone cement, for example, through the at least one port, to the distal region. In one embodiment, the at least one port, or each of the ports if more than one port is employed, includes an inlet, an outlet and a closed or substantially closed passageway there between, that is between the inlet and the outlet, in the device.

In some embodiments, the inlet of the at least one port is structured and positioned to receive bone cement, for example, from a cement injection system allowing delivery of cement, for example, from the proximal region or outside the proximal region, to the distal region, for example, while the implant is positioned on the prepared tibial surface.

Without wishing to limit the invention to any particular theory of operation, it is believed that the structure and/or location or position of the present at least one port of the present devices is useful in facilitating one or more benefits provided by the present devices, such as providing for enhanced passing of bone cement to an appropriate location between device and bone, enhanced containment of the bone cement, reduced leakage, for example, unwanted leakage, of bone cement around the periphery of the device or implant near the cement port at the bone implant interface, for example, into the joint space and/or reduced extrusion of the bone cement exterior of the device. For example, it is believed that the closed passageway between the inlet and outlet of the present port or ports provides better control of bone cement injection, bone cement containment or positioning between device and bone, bone cement leakage and/or bone cement extrusion outside the device relative to an identical prosthesis device in which the at least one port including a closed passageway is replaced by an open channel. The devices disclosed in Caspari et al U.S. Pat. No. 5,336,266, noted above, employ an open channel for injecting bone cement into the devices.

In one embodiment, the at least one port comprises two ports, for example, in a substantially side-by-side relationship, which generally extend through the device, for example generally through or adjacent a sidewall, for example, the peripheral sidewall and/or the distally extending sidewall. The port or ports may extend at an oblique or obtuse angle with respect to the support region. The ports may be located approximate a juncture of the straight sidewall portion and the curved sidewall portion of the device, for example, along the curved sidewall portion. In one embodiment of the invention, when the device has been implanted into the tibia bone, the inlet of at least one port is located at the anterior of the tibial component, for example, near the proximal region of the device.

The use of more than one port, for example, two ports, may be advantageous. For example, when a single port is used, the overall diameter of the port is greater for a given area of cement flow relative to using two smaller ports, for example, set side-by-side. Using such a side-by-side dual or two port system, for example, two substantially equally sized ports, allows for less bone resectioning and/or results in less trauma to the patient relative to using a device with a single port to provide the same area for cement flow.

The use of at least dual or two ports may allow the use of a double pronged insertion instrument to hold and/or manipulate the device or implant during surgery. A dual pronged instrument may provide a better grip and/or allow for finer control of the device or implant during surgery. Dual or two closed ports may allow irrigation and/or suction of the implant bone interface. Pulse lavage may be used effectively.

When the device is implanted into a tibia bone, the at least one port may be, and often is, located at an anterior region of the joint, for example, the knee joint.

In one embodiment, the distal region of the present device includes a support region comprising a fixation structure effective to enhance fixation of the device to a resurfaced region of a bone relative to an identical device without the fixation structure. The fixation structure may form a plurality of channels in the support region in communication with the at least one port. Thus, the bone cement introduced or injected through the port or ports may flow into and through the channels in facilitating fixation of the device to a resurfaced area of a bone. The fixation structure may comprise a plurality of undercuts or distally extending projections effective to facilitate bone cement from, for example, introduced or injected from, the at least one port, forming a cement bond, for example, an enhanced cement bond, between the device and a resurfaced region of a bone, for example, relative to an identical device without such undercuts or projections, such as an identical device having a support region with a featureless, planar distal surface.

In one embodiment, the channels in the support region may be formed by a appropriate positioning/ordering of the undercuts or projections. Therefore, a prosthetic device which includes both such channels and such undercuts or projections can be provided and is included within the scope of the present invention.

The present devices do not require that a through hole be provided for inserting a bone screw through the device into a tibia bone. In one embodiment, the present device includes no through hole, that is, the device is free of a through hole, for inserting a bone screw through the device into a tibia bone. This feature of the present devices facilitates maintaining the integrity of the bone remaining after the device is implanted, and reduces surgical trauma.

In some embodiments of the invention, the distal region includes a distally extending sidewall at least partially or even substantially entirely circumscribing the support region. A recess at least partially or even substantially entirely circumscribing the support region, for example, inside of the peripheral sidewall and/or distally extending sidewall, may be present. The recess may comprise a groove which at least partially or even substantially entirely circumscribes the support region. The peripheral sidewall/distally extending sidewall and recess provide structure effective to at least facilitate containment of bone cement used to secure the implant device to the resurfaced tibia bone, as well as prevent undesirable leakage of bone cement into the joint space.

In one advantageous aspect of the invention, one or both of the peripheral sidewall and the distally extending sidewall, for example, the distally extending sidewall, includes a flow control structure effective in controlling the flow of bone cement from the distal region. Such flow control structure is effective in enhancing the fixation of the present prosthesis device to the bone, for example, relative to an identical prosthesis device without the flow control structure. For example, the device may be structured to control flow of bone cement, that is to allow a limited or controlled flow of bone cement, for example, from the distal region, as discussed elsewhere herein, as well as prevent undesirable extrusion of bone cement exterior to the device, for example, into the joint space, after implantation of the device. The flow control structure, for example and without limitation, may include one or more notches and/or one or more sidewall grooves and/or one or more flow control ports into which the bone cement, for example, a limited or controlled amount of the bone cement, may enter to form an improved or enhanced bond, such as an improved or enhanced cement bond, between the bone, for example, the resurfaced region of the tibia bone, and the device.

Various embodiments of the present invention are described in detail in the detailed description and additional disclosure below. Any feature or combination of features described herein are included within the scope of the present invention provided that the features included in any such combination are not mutually inconsistent as will be apparent from the context, this specification, and the knowledge of one of ordinary skill in the art. In addition, any feature or combination of features may be specifically excluded from any embodiment of the present invention. Additional advantages and aspects of the present invention are apparent in the following detailed description, drawings, examples, and additional disclosure.

Many of the aspects and advantages of the present invention may be more clearly understood and appreciated with reference to the following Detailed Description and accompanying Drawings.

DETAILED DESCRIPTION

Turning now to the drawings, an exemplary embodiment of a tibial prosthesis device in accordance with the invention is shown generally at 10. The device 10 includes a curved peripheral wall or sidewall 16 and a generally straight peripheral wall or sidewall 18, which together form, in cross-section, a generally semi-circular shape, or a generally D-shape, which approximates a resurfaced area of a bone, for example, a resurfaced area of a tibia bone, on or into which the device is to be implanted.

Resurfacing of the tibia bone in preparation for implantation of tibial prosthesis device 10 may be performed using conventional techniques, for example conventional, open surgical techniques. In one embodiment, such preparation may be performed using the arthroscopic surgical devices and methods described in the co-pending U.S. provisional patent application Ser. No. 61/067,741, filed Feb. 29, 2008, entitled INSTRUMENTS AND METHOD FOR ARTHROSCOPY OF THE KNEE and commonly owned herewith, the entire disclosure of said application being incorporated herein by this specific reference.

Figure 1:
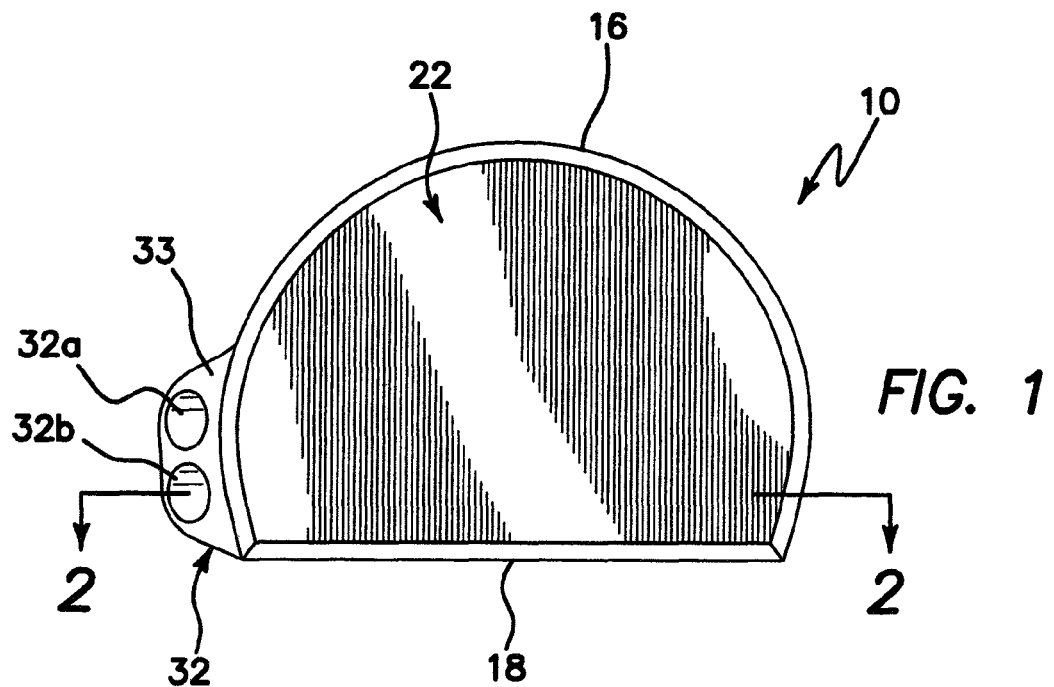
FIG. 1 is a top plan view of a tibial prosthesis device in accordance with the present invention showing a proximal region, for example, an articulating surface, of the device.
Figure 3:
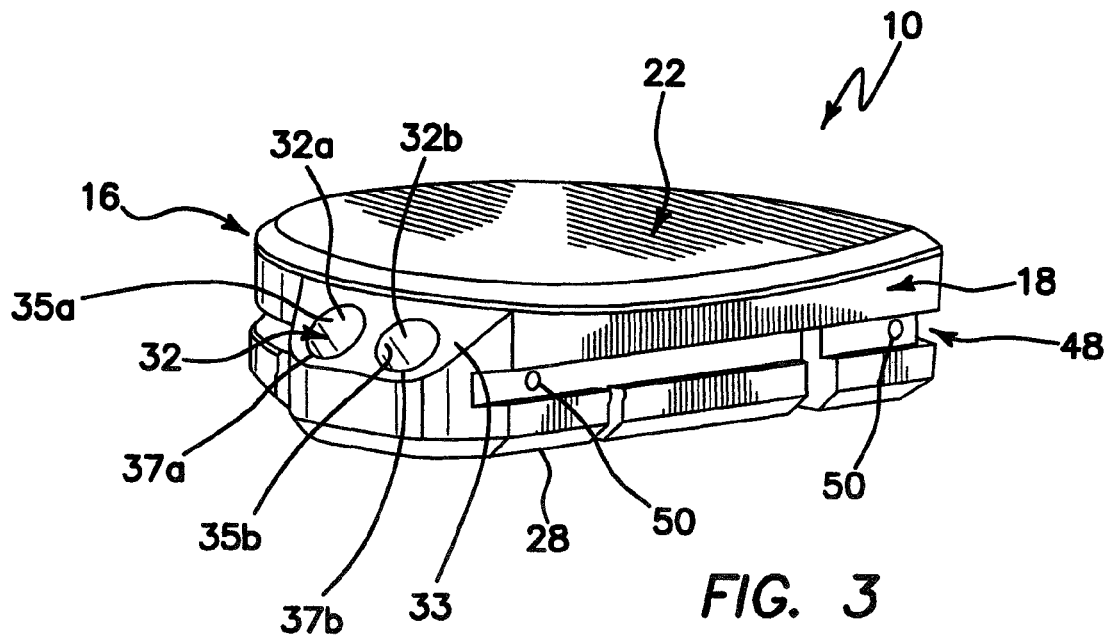
FIG. 3 is a perspective view of the device of FIG. 1 showing the proximal region of the device.
Figure 4:
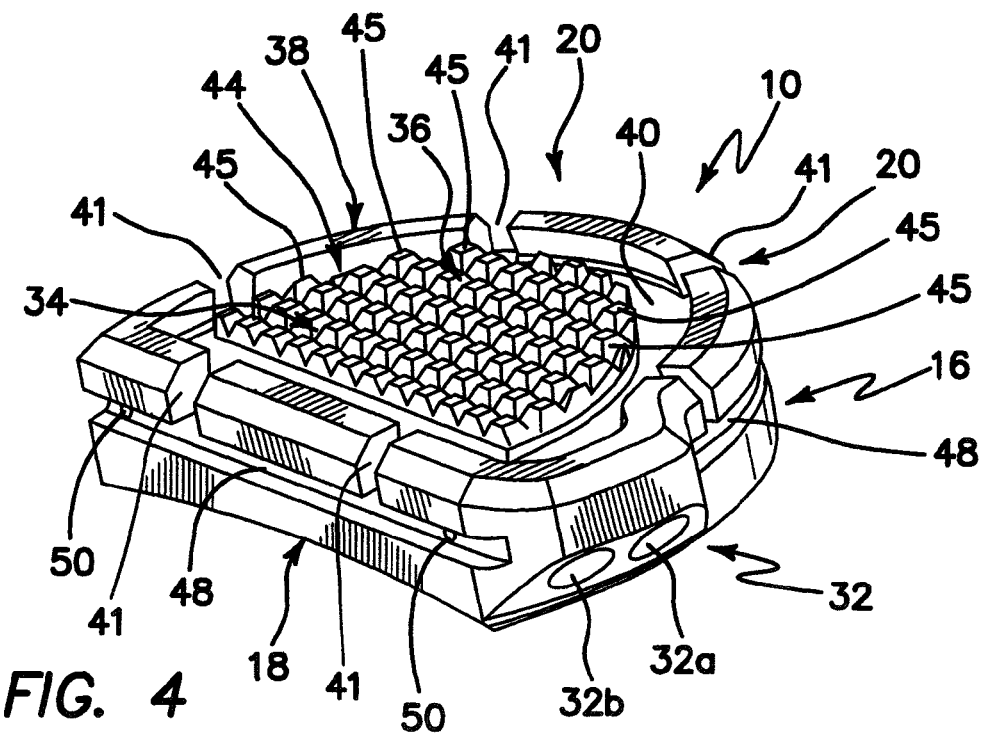
FIG. 4 is a perspective view of the device of FIG. 1 showing the distal fixation region, including the support region, of the device.
Figure 5:
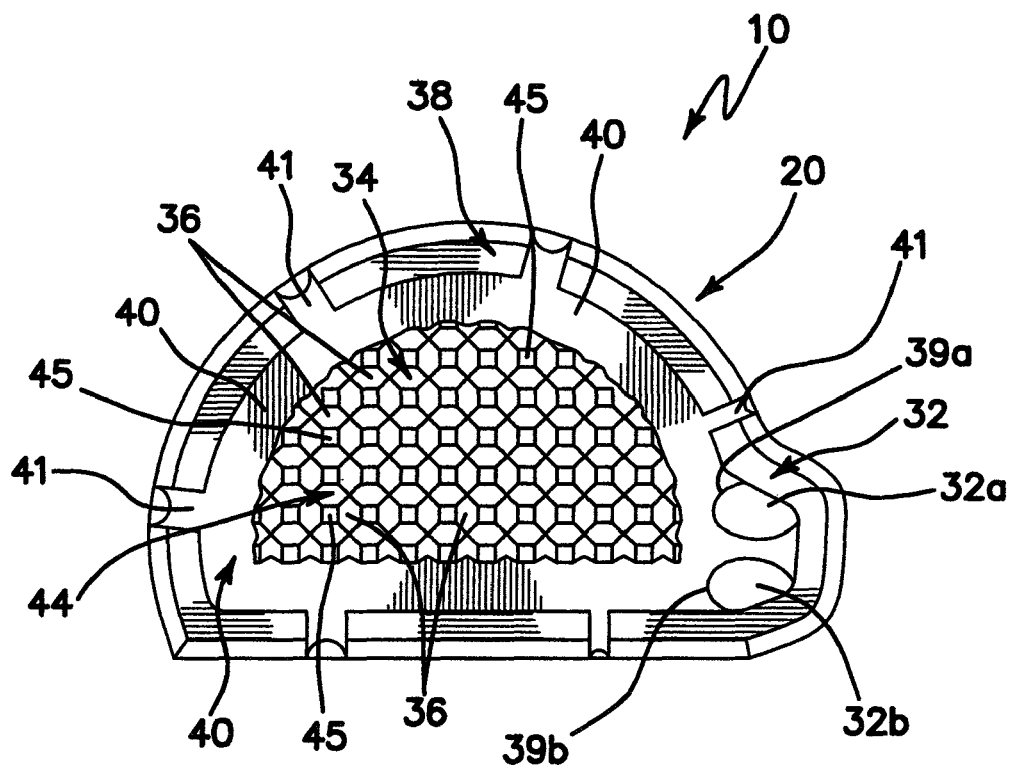
FIG. 5 is a bottom plan view of the device of FIG. 1 showing the distal fixation region of the device.

The device 10 further comprises a distal fixation region or distal region 20, shown perhaps most clearly in FIGS. 4 and 5, and a proximal articulating region or proximal region 22, shown in FIGS. 1 and 3. The distal region 20 is generally structured to interface with and be implanted onto or in a resurfaced region or area of a tibia bone. The proximal region 22 of the device 10, which substantially opposes the distal region 20, is slightly curved inwardly toward the center, for example, concave, and provides an articulating surface of the device 10, for example, with a femur bone or a femoral prosthesis device (not shown), after the device 10 is implanted on or into a resurfaced region of a tibia bone.

The distal region 20 includes a support region 34 comprising a fixation structure, shown generally at 44, for example, a regular or irregular fixation structure, effective to enhance fixation of the device 10 to a resurfaced region of a tibia bone relative to an identical device without the fixation structure. For example, the support region 34, and the fixation structure 44 in particular, comprise a system or network or plurality of undercuts or distally extending projections 45 and channels 36. For example, the plurality of undercuts or projections 45 form the channels 36. In the shown embodiment, some of the channels 36 are positioned substantially parallel to each other and some of the channels are substantially perpendicular to each other.

In any event, the fixation structure 44 is effective so that when bone cement, for example, bone cement in a fluid state, is introduced or injected into the distal region 20, in particular the support region 34, for example, through the ports 32, discussed hereinafter, while the device 10 is located in or on a resurfaced region of a tibia bone, an enhanced cement bond between the device 10 and the tibia bone is obtained.

Without wishing to limit the invention to any particular theory of operation, it is believed that the fixation structure 44, such as the channels 36/undercuts or projections 45 of fixation structure 44 shown in the drawings, provides the support region 34 with an increased amount of surface area, for example, relative to a substantially planar support region. Such increased surface area provides more area for the cement to bond with the device 10 and, ultimately, provides for an enhanced cement bond, for example, a cement bond of increased strength, between the device 10 and the tibia bone, for example, relative to an identical device having a planar support region.

Bone cement useful with the present invention may be any suitable bone cement known to those of skill in the art. For example, the bone cement may be a grout-like material, such as polymethyl methacrylate material and/or other suitable biocompatible material known to those of skill in the art which is effective to provide long term, for example, permanent or substantially permanent, fixation of a prosthesis to a surface of a bone.

In one especially advantageous aspect of the present invention, the device 10 is structured to be effective to facilitate introduction or injection and containment of bone cement during the surgical implantation procedure.

For example, in the shown embodiment, the device 10 further comprises structure for facilitating introduction of bone cement to the distal region 20. The device 10 comprises a port structure, shown generally at 32, including at least one port, for example, two ports 32a and 32b, for facilitating introduction or injection of bone cement to the distal region 20. The ports 32a and 32b are defined by bores extending through a surface region, for example, an angled surface region 33, of port structure 32, which extends outwardly and distally from the proximal region 22 of the device 10. The ports 32a and 32b include closed passageways defined by closed bore sidewalls 35a and 35b, respectively, between inlets 37a and 37b, respectively, and outlets 39a and 39b (FIG. 5), respectively.

In this embodiment, the ports 32a and 32b are disposed substantially directly adjacent one another, for example, in a substantially side-by-side relationship. The ports 32a and 32b are appropriately sized and positioned to facilitate introduction or injection of a suitable bone cement in a suitable amount to the bone/implant interface during surgical implantation of the device 10 on or into a resurfaced region of a tibia bone. Each of the ports 32a and 32b has an inlet 37a, 37b away from or outside of the distal region 20, and an outlet 39a, 39b through which bone cement passes to be placed in the distal region 20. Each of the ports 32a and 32b is oriented so that the closed passageway or bore 35a, 35b slants or slopes distally from the inlet to the outlet, for example, at an oblique or obtuse angle with respect to the support region 34. This orientation may facilitate injection of the bone cement and/or containment of the bone cement in the desired location or locations.

Figure 2:
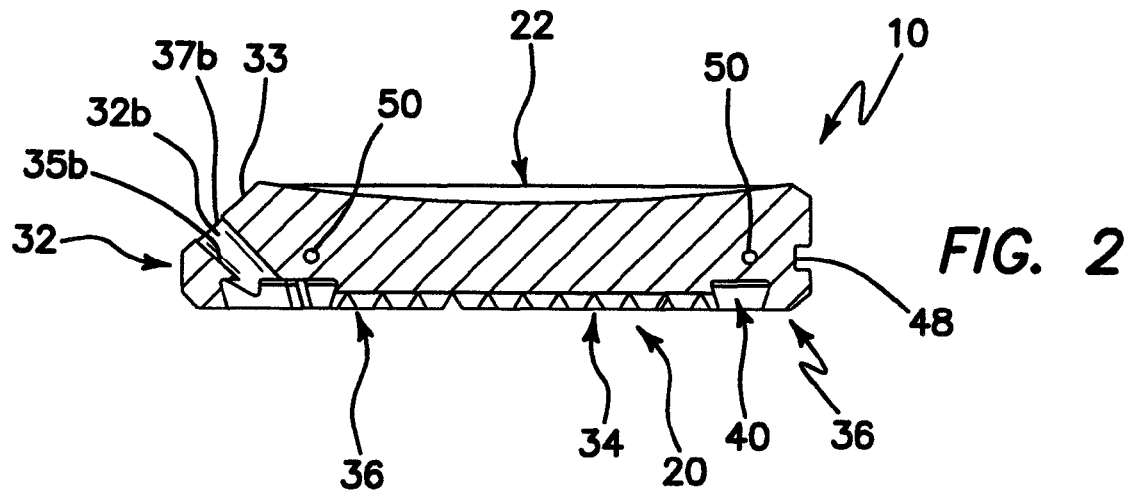
FIG. 2 is a cross-section of the device taken along line 2-2 of FIG. 1.

The ports 32a and 32b of the shown embodiment are located so that the inlets 37a and 37b are positioned outwardly from, and distally from the proximal region 22 of the device 10. The ports 32a and 32b are positioned to facilitate introduction or injection of bone cement to the distal portion 20. The ports 32a and 32b may have any of various geometric shapes and may pass through the device 10 at an oblique or obtuse angle relative to the support region 34, for example, as shown in FIG. 2.

The ports 32a and 32b may be positioned generally outside of the patella-tibial articulation region of the knee joint when the device 10 is implanted or affixed to the resurfaced region of a tibia bone. The ports 32a and 32b, in particular the inlets 37a and 37b of such ports, are located on angled surface 33, which is positioned in proximity to the intersection of substantially straight sidewall 18 and substantially curved sidewall 16 of the device 10. The angled surface 33 extends outwardly from the sidewalls 16 and 18. In one embodiment, the angled surface 33 may be joined at least partially or substantially entirely to the curved sidewall 16.

Although two ports 32a and 32b are shown in the drawings, in other embodiments of the invention not shown, the device 10 may comprise only one port or, alternatively, three or more ports. All such embodiments are included within the scope of the present invention.

The introduction or injection of the bone cement or bone cement material may be achieved through a pressurizing syringe or similar fluid mover. The bone cement injected may be a highly viscous material or a less viscous or a more fluid material, for example, relative to the highly viscous bone cement material conventionally introduced to bond an implant to bone. Injecting a more fluid material, such as a material which is flowable or readily flowable at normal or atmospheric pressure under the influence of gravity, is different from injecting highly viscous material, which is not readily flowable at such conditions. In one embodiment, the fluid or more fluid bone cement material has a viscosity (at room temperature) in a range of about 5,000 centipoise or less to about 50,000 centipoise or about 100,000 centipoise. The injected fluid bone cement material has increased effectiveness, for example, relative to highly viscous bone cement material, for example, injected highly viscous bone cement material, in filling interstitials or small regions between the prosthesis device and the bone, and/or in bonding with mating surfaces.

In the past, a surgeon often had to wait a period of time for the bone cement to set-up or harden sufficiently to allow the surgeon to handle the cement effectively. Such "set up" bone cement, once applied, tends to have or has reduced bonding ability.

The present invention allows the surgeon to take advantage of bone cement in a more fluid state. Such more fluid bone cement material, for example, more fluid bone cement material injected through one or more ports including closed passageways in the present prosthesis device, allows the pores in the bone to be filled with bonding material, as well as providing more adhesive properties to the implant itself. A marked or substantial increase in cement bond strength relative to conventional thumb packing techniques with "set up" bone cement have been shown when more fluid bone cement material is injected, for example, using the prosthesis devices of the present invention.

In the shown embodiment, the distal region 20 further comprises a distally extending flange or sidewall 38. Flange or sidewall 38 may be defined or considered as a distally extending portion of, and/or may be contiguous with, curved sidewall 16 and/or the straight sidewall 18. The distally extending flange or sidewall 38 may substantially entirely circumscribe the recess 40. The distally extending flange or sidewall 38 includes a flow control structure effective in providing for an amount, for example, a controlled or limited amount, of bone cement to flow from the distal region 20. For example, the flow control structure may include a plurality of spaced apart, open ended notches 41 in distally extending flange 38 for receiving bone cement to form additional bonding regions between the device 10 and the resurfaced region of a tibia bone about the outer periphery of the device 10.

The distal region 20 further includes a groove or recess 40, which may substantially entirely circumscribe the support region 34. The recess 40 may be flush with and/or otherwise in communication with the notches 41. This recess 40 provides additional space or volume in the distal region 20 for the introduction and containment of bone cement, which may result in an enhanced cement bond between the device 10 and the tibia bone. Since the recess 40 is in communication with the notches 41, the recess provides a supply of bone cement to be received in the notches 41. In general, recess 40 is effective in controlling the placement and containment of the bone cement introduced into the distal region 20 and in reducing the risk of undesirable leakage of the bone cement from the device 10 into the joint space.

Figure 6:
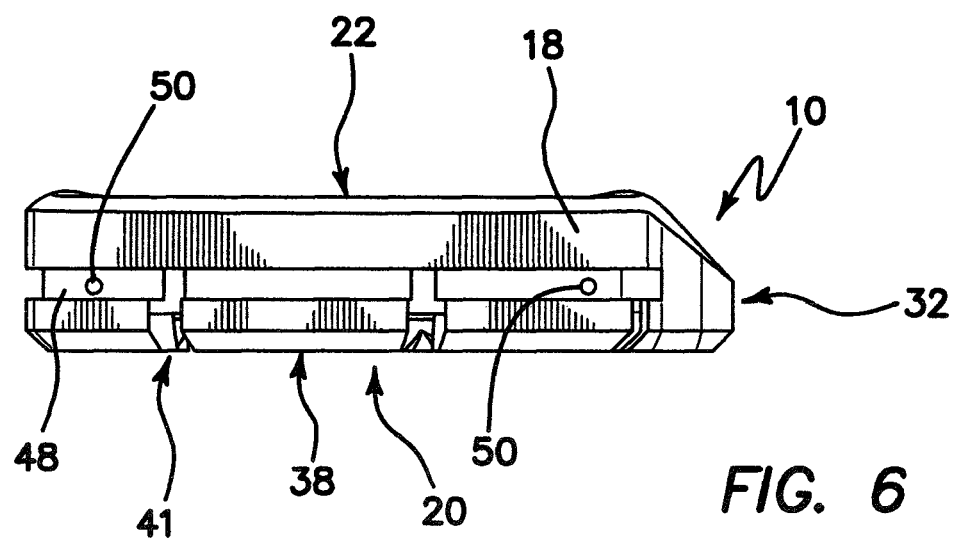
FIG. 6 is a side elevational view of the device.

The flow control structure, in the shown embodiment, includes open sidewall groove 48. Open sidewall groove 48 in the outside of sidewall 18, shown most clearly in FIG. 3 and FIG. 6, is in communication with notches 41 and is positioned and structured to be effective to facilitate the introduction of, placement of and/or containment of bone cement used to bond the device 10 to a resurfaced region of the tibia bone by permitting bone cement, for example, a controlled or limited amount of bone cement, extruded through the notches 41 from the distal region 20 to flow around the outer periphery of the device 10.

In one embodiment, the sidewall groove 48 can be segmented into a plurality, that is two or more, spaced apart sidewall groove segments, for example, separated from each other by portions of the peripheral sidewall/distally extending sidewall without the sidewall groove. Such embodiment is included within the scope of the present invention.

The flow control structure of device 10 includes control bores or flow control bores 50. Flow control bores 50 provide additional bone cement passageways between the distal region 20, for example, the recess 40 of the distal region, and the sidewall groove 48. Such control bores 50 are effective in controlling the placement of bone cement around the outer periphery of the device 10 when the device is implanted on or into a tibia bone.

The flow control structure in accordance with the present invention may include any one or more of the notches 41, the sidewall groove 48 and the flow control bores 50.

As shown in the drawings, the device 10 is a single unitary structure and has no moving parts. The device 10 may be made of a durable, biocompatible material. The device 10 may be made from a polymeric material, for example, any suitable polymeric material. Examples of suitable materials include ultra high molecular weight polyethylene (UHMWPE), for example, cast conforming to ASTM F75 Specification. The device 10 may be present in any suitable size or sizes.

Reference to the following U.S. patents and Published patent applications may provide additional disclosure which may be helpful in understanding one or more aspects of the present invention, each of said patents and publications being incorporated herein in its entirety by this specific reference: Bokros, U.S. Pat. No. 4,166,292; Matthews et al., U.S. Pat. No. 4,778,473; Hofmann et al., U.S. Pat. No. 4,963,152; Caspari et al., U.S. Pat. No. 5,171,276; Clark et al., U.S. Pat. No. 5,266,075; Clark et al., U.S. Pat. No. 5,393,302; Coates, U.S. Pat. No. 5,405,395; Clark, U.S. Pat. No. 5,643,273; Oudard et al., U.S. Pat. No. 5,766,256; Clark, U.S. Pat. No. 5,954,747; Clark et al., U.S. Pat. No. 6,306,138; Clark, U.S. Pat. No. 6,306,156; Musset et al., U.S. Pat. No. 6,423,096; Clark et al., U.S. Pat. No. 6,558,389; Johnson et al., U.S. Pat. No. 6,723,102; Clark et al., U.S. Pat. No. 6,780,188; Masini, U.S. Pat. No. 6,821,300; Sonnabend et al., U.S. Pat. No. 6,884,246; Carson et al., U.S. Pat. No. 6,923,817; Fell et al., U.S. Pat. No. 6,966,928; McCue et al., U.S. Pat. No. 7,083,652; Lipman et al., U.S. Pat. No. 7,105,027; Rosa et al., U.S. Pat. No. 7,141,053; Johnson et al., U.S. Pat. No. 7,297,164; Hayes, JR, et al., U.S. Publication No. 2002/0161448; Metzger et al., U.S. Publication No. 2003/0009232; Walker et al., U.S. Publication No. 2004/0243134; Walker et al., 2005/0192583; Walker et al., U.S. Publication No. 2005/0192584; Bernero et al., U.S. Publication No. 2006/0052875; Saadat et al., U.S. Publication No. 2007/0213735; Justin et al., U.S. Publication No. 2007/0288029.

While this invention has been described with respect to various specific examples and embodiments, it is to be understood that the invention is not limited thereto and that it can be variously practiced.

What is claimed is:

1. A tibial implant device useful in knee replacement surgery, the device comprising:
   a body having a concave proximal articulating region, a distal fixation region substantially opposing the proximal region and structured to interface with a resurfaced region of a tibia bone, and a peripheral sidewall between the proximal region and the distal region and including a curved sidewall portion and a substantially straight sidewall portion;
   a support region formed on said distal region, said support region including a plurality of distally extending projections which form a plurality of open channels for the passage of a flowable bone cement; and
   at least one port including an inlet, an outlet and a closed passageway there between in the device, the at least one port extending through an angled surface region, which angled surface region extends outwardly and distally from the proximal region, the at least one port being oriented so that the closed passageway slopes distally from the inlet to the outlet at an angle with respect to the support region, the at least one port being structured and positioned to allow flowable bone cement to be passed from outside the device through the closed passageway into the distal region after the device is placed in contact with a tibia bone;
   wherein the distal region further includes a distally extending sidewall at least partially circumscribing the support region, said distally extending sidewall including a flow control structure effective in controlling the flow of bone cement from the distal region; the flow control structure formed at least in part on the outer surface of the distally extending sidewall and including a plurality of spaced apart, open ended notches in the distally extending sidewall;
   wherein the device is single unitary structure, and is free of a through hole for inserting a bone screw through the device into a tibial bone.

2. The device of claim 1 wherein the at least one port comprises at least two ports spaced apart from the proximal region.

3. The device of claim 1 wherein the at least one port comprises two ports in a substantially side-by-side relationship.

4. The device of claim 1 wherein the at least one port extends at an oblique angle with respect to the support region.

5. The device of claim 1 which is made substantially entirely of polymeric material.

6. A tibial implant device useful in knee replacement surgery, the device comprising:
   a body having a concave proximal articulating region, a distal fixation region substantially opposing the proximal region and structured to interface with a resurfaced region of a tibia bone, and a peripheral sidewall between the proximal region and the distal region and including a curved sidewall portion and a substantially straight sidewall portion;
   at least one port including an inlet, an outlet and a closed passageway there between, the at least one port extending through an angled surface region, which angled surface region extends outwardly and distally from the proximal region, the at least one port being oriented so that the closed passageway slopes distally from the inlet to the outlet at an angle with respect to the support region, the at least one port structured and positioned to facilitate introduction of flowable bone cement from outside the device through the closed passageway into the distal region after the device is placed in contact with a tibia bone; and
   the distal region including a support region comprising a fixation structure effective to enhance fixation of the device to a resurfaced region of a tibia bone relative to an identical device without the fixation structure, the support region including a plurality of distally extending projections which form a plurality of open channels for the passage of flowable bone cement;

wherein the distal region further includes a distally extending sidewall at least partially circumscribing the support region, said distally extending sidewall including a flow control structure effective in controlling the flow of bone cement from the distal region; the flow control structure formed at least in part on the outer surface of the distally extending sidewall and including a plurality of spaced apart, open ended notches in the distally extending sidewall;

wherein the device is single unitary structure, and is free of a through hole for inserting a bone screw through the device into a tibial bone.

7. The device of claim 6 wherein the at least one port comprises two ports in a substantially side-by-side relationship.

8. The device of claim 6 wherein the flow control structure further includes at least one open sidewall groove along the outer surface of the distally extending sidewall, the at least one sidewall groove being in communication with at least one of the open ended notches.

9. The device of claim 8 wherein the flow control structure further comprises at least one control bore positioned and effective to provide a passageway for bone cement between the distal region and the at least one groove.

10. The device of claim 6 wherein the distal region further includes a recess at least partially circumscribing the support region.

11. The device of claim 6 which is made substantially entirely of polymeric material.

* * * * *